(12) United States Patent
Moran (10) Patent No.: US 6,423,744 B2
(45) Date of Patent: Jul. 23, 2002

(54) METHOD OF DIMINISHING THE ADVERSE EFFECTS OF INTERLEUKIN-2

(75) Inventor: Stanford Mark Moran, Orinda, CA (US)

(73) Assignee: Biomedicines, Inc., Emeryville, CA (US)

( * ) Notice: Subject to any disclaimer, the term of this patent is extended or adjusted under 35 U.S.C. 154(b) by 0 days.

(21) Appl. No.: 09/932,011

(22) Filed: Aug. 16, 2001

Related U.S. Application Data (63) Continuation-in-part of application No. 09/334,276, filed on Jun. 16, 1999, now abandoned.
(60) Provisional application No. 60/098,341, filed on Aug. 28, 1998.

(51) Int. Cl.$^7$ ..................... A61K 31/353; C07D 311/78
(52) U.S. Cl. ........................................ 514/456; 549/408
(58) Field of Search ........................... 514/456; 549/408

(56) References Cited

U.S. PATENT DOCUMENTS

| | | | |
|---|---|---|---|
| 4,665,203 A | 5/1987 | Miyano et al. | |
| 4,788,214 A | 11/1988 | Cohen et al. | |
| 4,889,871 A | 12/1989 | Djuric et al. | |
| 5,593,671 A | 1/1997 | Kerwar et al. | |

OTHER PUBLICATIONS

Misra, et al., In vitro and in vivo effect of diethylcarbamizine on the activity of acetylcholinesterase from *Wucheria bancrofti* infected human serum, *Trop. Med. Parasitol.*, Jun.;43(2), pp. 95–97 (1992).

Hunsinger, et al., Studies on the acute lethality of diethylcarbamazine in the rat, *Vet. Hum. Toxicol.*, 35(1): 11–5 (1993).

Kanesa–Thasan, et al., Diethylcarbamazine inhibits endothelial and microfilarial prostanoid metabolism in vitro, *Mol. Biochem. Parasitol.*, 49(1): 11–9 (1991).

Fujimaki, et al., Diethylcarbamazine, antifilarial drug, inhibits microtubule polymerization and disrupts preformed microtubules, *Biochem. Pharmacol.*, 39(5): 851–6 (1990).

Davidson and Drafta, Prolonged pulmonary hypertension caused by platelet–activating factor and leukotriene C4 in the rat lung, *J. Appl. Physiol.*, 73(3): 955–61, 1992.

Cotran, et al., *Pathologic Basis of Disease*, 6th Ed., W.B. Sounders & Co.,pp. 70–72, (1999).

Goodman & Gilman's, *The Pharmacological Basis of Therapeutics*, 9th Ed., McGraw Hill, pp. 601–616, (1996).

Edwards et al., "Interleukin 2 Acutely Reduces Platelet and Neutrophil–Endothelial Adherence and Macromolecular Leakage," Cancer Research, vol. 52, pp. 3425–3431, 1992.

Klausner et al., "Interleukin–2–Induced Lung Permeability is Mediated by Leukotriene $B_4$," Cancer, vol. 66, pp. 2357–2364, 1990.

Spiro et al., "Inhibition of Post–Translational Modification and Surface Expression of a Melanoma–Associated Chondroitin Sulfate Proteoglycan by Diethylcarbamazine or Ammonium Chloride," J. Biol. Chem., vol. 261, pp. 5121–5129, 1986.

Staub et al., "Preparation of Chronic Lung Lymph Fistulas in Sheep," J. Surg. Res., vol. 19, pp. 315–320, 1975.

Vetto et al., "Reduction of Toxicity of Interleukin–2 and Lymphokine–Activated Killer Cells in Humans by the Administration of Corticosteroids," J. Clin. Oncol., vol. 5, No. 3, pp. 496–503, 1987.

*Primary Examiner*—T. A. Solola
(74) *Attorney, Agent, or Firm*—Cooley Godward LLP (57) ABSTRACT

A method and composition for preserving or enhancing the beneficial effects of interleukin-2 (IL-2) while simultaneously mitigating the adverse effects of IL-2 on a subject is disclosed. The method involves administering an amount of a leukotriene $B_4$ ($LTB_4$) antagonist, preferably a $LTB_4$ receptor antagonistic, to a subject exhibiting adverse pharmacological effects due to exogenous IL-2, where the amount administered to the subject is sufficient to decrease the IL-2 induces adverse effects. Also disclosed is an article of manufacturing comprising a composition of the leukotriene $B_4$ antagonist in combination with labeling instructions for treatment. Also disclosed is a method for preparing a pharmaceutical composition. Generally the $LTB_4$ antagonist will reduce the IL-2-induced adverse effects while preserving or enhancing the antitumor, antiviral, or immunostimulatory effects of IL-2, thereby improving the therapeutic index of IL-2.

27 Claims, 2 Drawing Sheets

METHOD OF DIMINISHING THE ADVERSE EFFECTS OF INTERLEUKIN-2

CROSS REFERENCE

This is a continuation-in-part of U.S. Ser. No. 09/334,276, filed Jun. 16, 1999, now abandoned which in turn claims priority to and is a continuation-in-part of U.S. Ser. No. 60/098,341, filed Aug. 28, 1998. Both applications are incorporated herein by reference.

INTRODUCTION

1. Technical Field

This invention relates to mitigating adverse effects induced by interleukin-2 through the administration of an effective amount of a leukotriene $B_4$ antagonist.

2. Background

Recombinant interleukin-2 (PROLEUKIN® or "IL-2") is an analogue of human native interleukin-2. While human native interleukin-2 is present in a human in small amounts, under certain conditions, i.e., the administration of IL-2 to treat certain conditions, excess levels (i.e., higher than normal levels) of IL-2 will be present in a subject's system. IL-2 is approved for the treatment of certain human malignancies including melanoma and renal cell carcinoma and is useful in treating certain viral conditions. IL-2 is thought to work by stimulating the immune system to work as an antitumor or antiviral agent. It can be viewed as having antitumor, antiviral, and immunostimulating activity. The administration of IL-2 has been associated with "vascular leak syndrome" (VLS), which results from extravasation of plasma proteins and fluid into the extravascular space. It is known that, among other adverse signs or symptoms, VLS can cause generalized edema, systemic hypotension, reduced organ perfusion, and subsequent dysfunction of one or more organs. When sufficiently severe, VLS may cause significant disability or even death. The adverse effects of IL-2 may necessitate using a lower dose of IL-2, thereby diminishing the potential for therapeutic benefit from IL-2. An effective means of mitigating IL-2 toxicity would be beneficial.

Empirical approaches to treating VLS have included the use of corticosteroids, which, unfortunately, can reduce the antitumor effects of IL-2. The pluripotent filaricide diethylcarbamazine (DEC) has also been studied experimentally, but because of its diverse pharmacological effects, the specific role of DEC in VLS is unclear. DEC is known to be a 5-lipoxygenase inhibitor. The antifolate methotrexate has also been suggested as a means of mitigating VLS. Unfortunately, methotrexate itself is quite toxic.

However, blocking the adverse effects of any substance, e.g. IL-2, may also block the beneficial effects. It is a deficiency of prior art that no intervention to prevent or mitigate VLS has been shown not to interfere with the antitumor activity or, more preferably, to enhance the antitumor activity of interleukin-2.

It is generally known that 5-lipoxygenase is instrumental in initiating production of 5-hydroperoxyeicosatetraenoic acid (HPETE) and leading to the production of 5-HETE, $LTA_4$, $LTB_4$, $LTC_4$, $LTD_4$, and $LTE_4$. See Figure 3-18 at page 71 of Robbins, *Pathologic Basis of Disease*, 6th Ed. By Ramzi S. Kotran, M.D.; Vinay Kumar, M.D., FRC Path.; and Tucker Collins, M.D., Ph.D., W. B. Saunders & Co. (1999). This Chapter also establishes that $LTC_4$, LTD4, and $LTE_4$ have an action of elevating vascular permeability, but not $LTB_4$. (See Table 3-4). See Goodman & Gilman's, *The Pharmacological Basis of Therapeutics*, 9th Ed., McGraw Hill (1996), pp. 601–616. On cell activation and intracellular $Ca^{2+}$ increases, 5-lipoxygenase binds to a 5-lipoxygenase activating protein (FLAP). This binding activates the 5-lipoxygenase which results in its association with the cell membrane and increased synthesis of 5-HPETE. The 5-HPETE is rearranged by LTA synthase to an unstable 5,6-epoxide, known as $LTA_4$. $LTA_4$ may be transformed by LTA hydrolase to $LTB_4$. Alternatively, it may be conjugated with glutathione by $LTC_4$ synthase to form $LTC_4$. $LTC_4$ may be transformed to $LTD_4$ by the removal of glutamic acid. $LTD_4$ may in turn be converted to $LTE_4$ by the cleavage of glycine. The reincorporation of glutamic acid to $LTE_4$ yields a γ-glutamylcysteinyl derivative called $LTF_4$.

Thus, a 5-lipoxygenase inhibitor would be expected to decrease production of 5-HPETE (and 5-HETE), $LTA_4$, $LTB_4$, $LTC_4$, $LTD_4$, and $LTE_4$.

As the variety of potential interventions suggests, the pathogenesis of VLS is unknown. It has been demonstrated, however, that IL-2 increases plasma levels of leukotriene $B_4$. I have found that using a leukotriene $B_4$ receptor antagonist (LA), preferably a leukotriene $B_4$ antagonist, during IL-2 therapy mitigates VLS and lessens the adverse effects of IL-2 while preserving or enhancing the beneficial effect of IL-2.

Thus, evidence shows that specific blockade of the leukotriene $B_4$ receptor not only mitigates VLS and lessens the adverse effects of IL-2 but it also preserves or enhances antitumor, antiviral, or immunostimulatory activity, thereby improving the therapeutic index of IL-2. The improved therapeutic index of IL-2 leads to several advantages. These include

- reducing diagnostic testing required to
  - i. enhance tumor response to IL-2 by permitting a higher number of doses or a larger dosing amount of IL-2 with no significant increase in adverse effects induced by IL-2
  - ii. monitor patient responses to IL-2
  - iii. determine the success of therapeutic interventions required to mitigate IL-2 related adverse events
  - iv. demonstrate that certain events are caused by IL-2 rather than another agent
- obviating or reducing the need to place patients into intensive care units or onto respirators in the case of severe pulmonary edema,
- obviating or reducing the need to place patients into cardiac or coronary care units in the case of severe arrhythmia or congestive heart failure,
- obviating the need for placing patients onto dialysis protocols the case of renal compromise,
- reducing the need for intensive nursing or support care.
- reducing or obviating the use of medications or other devices for prevention or treatment of adverse effects expected or caused by IL-2

All of these advantages should then lead to better tolerated treatment, reduced overall cost of treatment and better response to treatment.

SUMMARY OF THE INVENTION

One aspect of this invention is a method of mitigating an adverse pharmacological effect of IL-2 in a subject. The method comprises administering to a subject receiving exogenous IL-2 an amount of a leukotriene $B_4$ inhibitor or antagonist (preferably a leukotriene $B_4$ receptor antagonist) that is sufficient to mitigate the adverse effects. Another aspect is treating a malignancy or viral infection in a mammal by administering a therapeutically effective amount of IL-2 in combination with a leukotriene $B_4$ antagonist in an amount sufficient to reduce IL-2-induced adverse pharmacological effects, e.g., increased vascular permeability. Another aspect is simultaneously preserving or enhancing the antitumor, antiviral, or immunostimulatory activity of IL-2.

The preferred leukotriene $B_4$ receptor antagonist is represented by the Formula (I), or a stereoisomer or pharmaceutically acceptable salt thereof, wherein $R^1$ represents alkyl having 2 to 6 carbon atoms, alkenyl having 2 to 6 carbon atoms, alkynyl having 2 to 6 carbon atoms, or $(CH_2)_nR$ wherein R represents cycloalkyl of 3 to 5 carbon atoms and n is 1 or 2;

$R^2$ represents hydrogen, methyl or ethyl;

$R^3$ represents alkyl having 1 to 5 carbon atoms;

W represents a bridging group such as $(CH_2)_x$ where x is 2 to 7, alkenylene having 3 to 7 carbon atoms, alkynylene having 3 to 7 carbon atoms or cyclopentyl;

$R^4$ represents hydrogen, alkyl having 2 to 5 carbon atoms, alkynyl having 2 to 5 carbon atoms, alkenyl having 2 to 5 carbon atoms, alkanoyl of 2 to 5 carbon atoms, or aralkanoyl of 7 to 9 carbon atoms;

$R^5$ represents hydrogen, alkyl having 1 to 6 carbon atoms, or $R^5$ represents alkanoyl having 2 to 4 carbon atoms, or $(CH_2)_y$—$CO_2R^8$ wherein y is 0 to 4 and $R^8$ is hydrogen or alkyl having 1 to 6 carbon atoms;

$R^6$ represents hydrogen or together with $R^5$ represents a carbon to carbon bond; and A represents —Z—$CO_2R^7$ wherein $R^7$ represents hydrogen or alkyl having 1 to 6 carbon atoms, and wherein Z is absent or represents straight or branched chain alkylene or alkenylene having up to 6 carbon atoms.

Other leukotriene $B_4$ receptor antagonists include those set forth in U.S. Pat. No. 4,788,214 (which is incorporated herein by reference), BIIL-284 and ebselen (DR-3305) as further described herein.

Another aspect of the invention may be viewed as an improvement in a method of treatment. In a method of treating a malignancy or viral infection or immunological disorder in a mammal, which method comprises administering a therapeutically effective amount of IL-2, which administration also induces adverse pharmacological effects in the mammal, the improvement comprises administering a leukotriene $B_4$ antagonist in an amount sufficient to mitigate IL-2 induced adverse pharmacological effects, preferably while simultaneously preserving or enhancing the antitumor, antiviral, or immunostimulatory activity, of IL-2.

Another aspect of this invention is a process for preparing a pharmaceutical composition. The process comprises combining a leukotriene $B_4$ antagonist with a pharmaceutical excipient to form a composition useful for mitigating IL-2 induced adverse pharmacological effects in a subject receiving exogenous IL-2, preferably while simultaneously preserving or enhancing the antitumor or antiviral activity, or other desirable pharmacological activity, of IL-2.

Still another aspect of this invention is an article of manufacture that comprises a pharmaceutical composition comprising a leukotriene $B_4$ antagonist as a unit dosage in combination with instructions for administering the composition to a mammal undergoing treatment of a malignancy or viral infection with IL-2, wherein the amount of the composition administered is sufficient to mitigate IL-2 induced adverse pharmacological effects in the mammal being treated, preferably while simultaneously preserving or enhancing the antitumor or antiviral activity, or other desirable pharmacological activity, of IL-2. Still another aspect of this invention is an article of manufacture that comprises packaging and labeling thereof such that a leukotriene $B_4$ antagonist, preferably a leukotriene $B_4$ receptor antagonist, is used in conjunction with IL-2 for the treatment of IL-2 responsive disorders.

In general, the $LTB_4$ antagonist, preferably the $LTB_4$ receptor antagonist, will reduce the adverse effects caused by IL-2 while simultaneously preserving or enhancing the antitumor, antiviral, and/or immunostimulatory effects of IL-2 or will reduce the IL-2-induced adverse effects more than any reduction in IL-2 related antitumor, antiviral, or immunostimulatory effects IL-2. The use of the $LTB_4$ antagonist can be said to improve the therapeutic index of IL-2.

DETAILED DESCRIPTION AND PRESENTLY PREFERRED EMBODIMENTS

For purposes of this application the following definitions apply:

Alkyl means a fully saturated hydrocarbon radical having the number of carbon atoms indicated. For example, alkyl of 1 to 6 includes, e.g., methyl, ethyl, n-propyl, i-propyl, n-butyl, i-butyl, t-butyl, n-pentyl, amyl, n-hexyl, and the like.

Alkenyl means a radical derived from an alkene, i.e., hydrocarbon having a single double bond and having the number of carbons indicated. For example, alkenyl of 2–6 carbon atoms includes radicals derived from ethylene, propylene, 1-butene, 2-butene, isobutylene, 3,3-dimethylpropylene, and the like.

Alkynyl means a radical derived from an alkyne, i.e., hydrocarbon having a single triple bond and having the number of carbons indicated. For example alkynyl of 1–6 carbon atoms includes acetylenyl, propynyl, 1-butynyl, 1 pentynyl, 1-hexynyl and the like.

Alkanoyl means a radical represented by the formula RC(O)— where R is alkyl of the number of carbons indicated.

Aralkanoyl means a radical represented by the formula ArC(O)— where Ar is an aryl group of the number of carbons indicated, e.g., phenyl (6 carbons).

LA is the abbreviation for leukotriene $B_4$ antagonist.

Pharmaceutically-acceptable salts are those that are physiologically acceptable for pharmaceutical purposes and include, e.g., ammonium, potassium, sodium, alkaline earth, and the like.

A stereoisomer is one of a set of isomers whose molecules have the same atoms bonded to each other but differ in the way these atoms are arranged in space. Included in this are enantiomers, i.e., compounds that are mirror images of each other but that are not superimposable upon each other.

It should be understood that the use of the alternative "or" with items in a series is meant to include both the alternative and the collective. Thus, "preserving the antitumor, antiviral, or immunostimulatory effects" would include preserving each alone or in any combination.

Compounds Useful in the Invention

An LA useful in this invention is one that blocks the effects mediated by the leukotriene $B_4$ receptor. An LA may block the effects mediated by the $LTB_4$ receptor by acting directly on the receptor or by inhibiting the synthesis of $LTB_4$, preferably the former. Non-limiting examples of $LTB_4$ antagonists include in BIIL-284 and ebselen. BIIL-284 is a drug being developed by Boehringer Engelheim in Germany. The structure of the compound is shown in formula (II) as follows:

Ebselen is being developed by Daiichi Pharmaceutical in Japan and is also known as DR-3305 and Harmokisane. It is an orally active organoselenium compound having the formula (III)

More information about these compounds may be found at Pharmaprojects, accession numbers 17685 and 5076.

A preferred class of compounds is represented by Formula (I) as set forth in the "Summary of the Invention" section of this application or a pharmaceutically acceptable salt thereof. In Formula (I), $R^1$ represents hydrogen, alkyl having 1 to 6 carbon atoms, alkenyl having 2 to 6 carbon atoms, alkynyl having 2 to 6 carbon atoms, or $(CH_2)_nR$ wherein R represents cycloalkyl of 3 to 5 carbon atoms and n is 1 or 2;

$R^2$ represents hydrogen, methyl or ethyl;

$R^3$ represents alkyl having 1 to 5 carbon atoms;

W represents $(CH_2)_x$ where x is 2 to 7, alkenylene having 3 to 7 carbon atoms, alkynylene having 3 to 7 carbon atoms or cyclopentylene;

$R^4$ represents hydrogen, alkyl having 2 to 5 carbon atoms, alkynyl having 2 to 5 carbon atoms, alkenyl having 2 to 5 carbon atoms, alkanoyl of 2 to 5 carbon atoms or aralkanoyl;

$R^5$ represents hydrogen, alkyl having 1 to 6 carbon atoms, or $R^5$ represents alkanoyl having 2 to 4 carbon atoms, or $(CH_2)_Y$—$CO_2R^8$ wherein $Y$ is 0 to 4 and $R^8$ is hydrogen or alkyl having 1 to 6 carbon atoms;

$R^6$ represents hydrogen or together with $R^5$ represents a carbon to carbon bond; and A represents —Z—$CO_2R^7$ wherein $R^7$ represents hydrogen or alkyl having 1 to 6 carbon atoms, and wherein Z is absent or represents straight or branched chain alkylene or alkenylene having up to 6 carbon atoms.

A preferred subgroup is represented by Formula (I) wherein $R^1$ represents alkyl having 2–4 carbon atoms; $R^2$ represents hydrogen, methyl or ethyl; $R^3$ represents alkyl having 1 to 3 carbon atoms; W represents $(CH_2)_x$ where x is 3 to 5, alkenylene having 3 to 5 carbon atoms, alkynylene having 3 to 5 carbon atoms, or cyclopentylene; $R^4$ represents alkyl having 2 to 4 carbon atoms, acetyl or benzoyl; $R^5$ represents hydrogen, or alkyl having 1 to 4 carbon atoms; and A represents —Z—$CO_2R^7$, wherein $R^7$ represents hydrogen or alkyl having 1 to 4 carbon atoms, and wherein Z is absent or represents alkylene having up to 2 carbon atoms; or a stereoisomer or pharmaceutically acceptable salt thereof of this subgroup. Particularly useful are compounds represented by Formula (I) wherein $R^1$ is n-propyl; $R^2$ and $R^3$ each is methyl; W is $(CH_2)_x$, where x is 3, 4 or 5; $R^4$ is n-propyl; $R^5$ represents hydrogen or alkyl of 1 to 4 carbon atoms; and A represents —Z—$CO_2R^7$ wherein $R^7$ represents hydrogen or alkyl having 1 to 4 carbon atoms and Z is absent or represents alkylene having up to 2 carbon atoms; or a stereoisomer or a pharmaceutically acceptable salt thereof. Particularly preferred is a leukotriene $B_4$ receptor antagonist as represented by Formula (I) wherein $R^1$ is n-propyl, $R^2$ and $R^3$ each is methyl, $R^4$ is n-propyl at the 8-position. W is $(CH_2)_3$; $R^5$ is H; and A is $(CH_2)_p$—COOH, where p is 0, 1 or 2, especially 0 or a stereoisomer or a pharmaceutically acceptable salt thereof.

Other compounds useful in this invention are set forth in U.S. Pat. No. 4,788,214.

The compounds represented by Formula (I) in which position 2 of the benzopyran ring is a chiral center exist in racemic form as a mixture of individual enantiomers (i.e., racemate), or as the pure individual enantiomers. Formula (I) is intended to cover the racemic mixture containing equal quantities of dextrorotatory (+) and levorotatory (−) enantiomers as well as the individual dextroratory enantiomer, the levorotatory enantiomer and other non-equal mixtures of enantiomers. The formula is to be interpreted as covering any stereoisomer of the compound.

Representative compounds include the following (or the corresponding pharmaceutically acceptable salts thereof or the stereoisomers):

7-[3-(4-acetyl-3-methoxy-2-propylphenoxy)propoxy]-3,4-dihydro-8-propyl-2H-1-benzopyran-2-carboxylic acid;

7-[[5-(4-acetyl-3-methoxy-2-propylphenoxy)pentyl]oxy]-3,4-dihydro-8-propyl-2H-1-benzopyran-2-carboxylic acid, ethyl ester;

7-[3-(4-acetyl-3-methoxy-2-propylphenoxy)propoxy]-3,4-dihydro-8-propyl-2H-1-benzopyran-2-propanoic acid;

7-[3-(4-acetyl-3-methoxy-2-propylphenoxy)propoxy]-3,4-dihydro-2-methyl-8-propyl-2H-1-benzopyran-2-propanoic acid;

7-[3-(4-acetyl-3-methoxy-2-propylphenoxy)propoxy]-3,4-dihydro-2-methyl-8-propyl-2H-1-benzopyran-2-propanoic acid, methyl ester;

7-[3-(4-acetyl-2-(cyclopropylmethyl)-3-methoxyphenoxy)propoxy]-3,4dihydro-8-propyl-2H-1-benzopyran-2-carboxylic acid;

7-[[5-(4-acetyl-3-methoxy-2-propylphenoxy)pentyl]oxy]-3,4-dihydro-8-propyl-2H-1-benzopyran-2-carboxylic acid;

7-[5-(4-acetyl-3-hydroxy-2-propylphenoxy)-pentyloxy]-6-acetyl-3,4-dihydro-2H-1-benzopyran-2-carboxylic acid; and 7-[5-(4-acetyl-3-hydroxy-2-propylphenoxy)-pentyloxy]-6-benzoyl-3,4-dihydro-2H-1-benzopyran-2-carboxylic acid.

Preparation of Compounds Useful in this Invention

These compounds, previously unknown for use with IL-2, are prepared by processes set forth in U.S. Pat. No. 4,889,871 issued Dec. 26, 1989 to Djuric, et al. and U.S. Pat. No. 4,788,214 issued Nov. 29, 1988 to Cohen et al. These patents are incorporated herein by reference in their entirety. The compounds useful in this invention are prepared by methods that result in the racemic compound or by stereospecific methods that result in the individual stereoisomers.

U.S. Pat. No. 4,665,203 issued May 12, 1987 discloses methods for making some of the intermediates used in making compounds of the present invention. The patent is incorporated herein by reference.

Preferred compounds useful in this invention, where $R^2$ is methyl or ethyl, are generally prepared by alkylating the prior art phenol hydroxy ($R^2$ is H) compounds to form compounds of Formula (I) by conventional techniques. Thus, the reaction of the phenol hydroxy ($R^2$ is H) with methyl iodide in potassium carbonate provides the ether. Dimethyl sulfate in acetone and base is also useful in preparing ethers. Alternatively, intermediates can be alkylated prior to forming the —O—$(CH_2)_x$—O— bridge. Hydrolysis of the ester compounds in the presence of lithium hydroxide and methanol gives the acid compounds.

The compounds of Formula (I) and those of U.S. Pat. No. 4,788,214 that contain an asymmetric carbon atom at position 2 of the benzopyran ring are normally obtained from the synthesis as racemic mixtures. Resolution of the racemates into the corresponding optically active isomers (enantiomers) can be carried out by persons skilled in the art using known procedures.

Compounds of Formula (I) when $R^7$ is hydrogen are carboxylic acids. A racemic mixture of a carboxylic acid may be resolved by first treating the racemate with an optically active amine base to form a mixture of diastereomeric salts. Examples of optically active amine bases that may be used for this purpose are (R)-(+)--methylbenzylamine, (S)-(−)--methylbenzylamine, (1R,2S)-(−)-ephedrine, quinine, and quinidine. The thusly formed diastereomeric salts have different properties, such as solubility, and the diastereomers may therefore be separated by selective recrystallization from a suitable solvent. The optically active carboxylic acids may then be obtained by re-acidification of the separated diastereomeric salts.

Alternatively, a racemic mixture of a carboxylic acid may be treated with an optically active alcohol to form a mixture of diastereomeric esters. Examples of optically active alcohols that may be used for this purpose are (1R,2S,5R)-(−)-menthol, (1S,2R,5S)-(+)-menthol, (R)-(−)-2-octanol, and (S)-(+)-2-octanol. The thusly-formed mixture of diastereomeric esters may then be separated by chromatography. The optically active carboxylic acids may then be obtained from the separated diastereomeric esters by conventional techniques, such as treatment of the esters with sodium hydroxide or lithium hydroxide followed by reacidification.

Compounds of Formula (I) when $R^7$ is alkyl are esters. A racemate of the esters may be resolved into the enantiomers by first resolving a racemic mixture of the corresponding carboxylic acid using one of the methods described above. The optically active ester may be obtained by esterification of the corresponding optically active carboxylic acid by procedures similar to those used to prepare a racemic ester.

Alternatively, a racemic mixture of a carboxylic acid of Formula (I) or a racemic mixture of an ester of Formula (I), may be separated into the individual enantiomers by high performance liquid chromatography using a suitable chiral stationary phase and a suitable eluent.

Administration of Compounds Useful in this Invention

An aspect of this invention is a method of mitigating an adverse pharmacological effect of IL-2 in a subject at risk of, or in fact exhibiting, such effect. The method comprises administering to a subject receiving IL-2 an amount of an LA, preferably a leukotriene $B_4$ receptor antagonist, that is sufficient to mitigate the adverse effects of the IL-2, preferably while preserving or enhancing the benefits of IL-2. Generally the excess IL-2 is a result of IL-2 (e.g., PROLEUKIN®) administration to treat a malignancy, acquired immunodeficiency syndrome (AIDS) or other malady.

To mitigate the adverse effects induced by IL-2 administration while preserving or enhancing benefits from IL-2 and thereby improving the therapeutic index of IL-2, a compound is delivered at a level sufficient to achieve both goals simultaneously. That amount will vary somewhat from subject to subject but generally will be in the range of about 0.1 mg to about 10.0 mg per kilogram of body weight per day. The preferred range is from 0.1 to 5.0 mg/kg/day while the most preferred range is from 1.0 to 5.0 mg/kg/day. Thus, for a 50 kg person, about 5.0 to 500 mg/day would be administered. For a 70 kg person about 7.0 to 700 mg/day.

In general, the adverse pharmacological effect of IL-2 in a subject will occur during or after the treatment of the subject for an IL-2-responsive disease state. Thus, the method, along with other aspects of the invention, is useful in treating a subject having a leukotriene $B_4$ receptor in its system. This generally includes mammals, such as livestock and pets, and particularly humans. Thus, this invention will find use in treating humans of all ages as well as in treating animals, i.e., in veterinary uses. The invention may be used for treating livestock such as cattle, sheep, pigs, goats, and the like or for treating household pets such as dogs, cats, rabbits, hamsters, mice, rats, and the like. The primary utility is for treating humans. IL-2 is administered to a human as part of the treatment of a malignant tumor, i.e., cancer, or a viral disease such as AIDS. The adverse pharmacological effect often seen in such treatment is increased vascular permeability, e.g., VLS. The signs and symptoms of the adverse pharmacological effect are, for example, cardiovascular (hypotension requiring pressors; arrhythmias, pericardial effusion); pulmonary (congestion, dyspnea, pulmonary edema, hypoxemia); hepatic (increased bilirubin, jaundice, ascites); hematologic (anemia, thrombocytopenia, leukopenia); gastrointestinal (nausea, emesis, diarrhea, gastrointestinal bleeding); renal (oliguria/anuria, decreased excretory function); dermatologic (pruritus, erythema, rash); musculoskeletal (arthralgia, myalgia); neural (dysfunction of central or peripheral nervous system, epileptic seizures); general (fever, pain, fatigue, weakness, localized or generalized edema, infection, weight gain, headache).

Thus, another aspect of this invention is a method of treating a malignancy or viral or immunological disease in a mammal, which method comprises administering a therapeutically effective amount of IL-2 in conjunction with the LA, as described herein, in an amount sufficient to mitigate IL-2-induced adverse physiological effects. The method may be performed by administering the IL-2 and the LA in combination as a unit dosage or the IL-2 and the LA may be administered individually, with the LA being administered before, during or after the administration of the IL-2. The LA may be administered by any suitable route of administration, preferably parenterally orally before, during or after the IL-2 is administered.

Another aspect of this invention is a method of treating a malignancy or viral or immunological disease in a mammal and improving the therapeutic index of treatment, which method comprises administering a therapeutically effective amount of IL-2 in conjunction with the LA, as described herein, in an amount sufficient to mitigate IL-2 induced adverse effects while preserving or enhancing the antitumor, antiviral, or immunostimulatory activity of IL-2. Those skilled in the art will recognize that this method will increase the therapeutic index of treatment.

Another aspect of this invention comprises administering a therapeutically effective amount of IL-2 in conjunction with the LA, as described herein, in an amount sufficient to reduce IL-2 adverse effects more than any reduction in antitumor, antiviral, or immunostimulatory effects, thereby also enhancing the therapeutic index of treatment.

Viewed another way, this invention may be seen as an improvement in a method of treating a malignancy or other malady requiring IL-2 treatment. The subject method comprises administering a therapeutically effective amount of IL-2. Because this treatment induces adverse pharmacological effects in the mammal, the improvement of this invention comprises administering the LA in an amount sufficient to mitigate IL-2 induced adverse pharmacological effects, preferably while preserving or enhancing the efficacy of IL-2.

Those skilled in the art will also recognize the current invention would also be useful when a chemically or biologically modified form of interleukin-2 is employed, wherein such modification in itself is intended to reduce the adverse effects of interleukin-2.

Human recombinant interleukin-2 is a well-studied, well-characterized and effective antineoplastic drug with well documented, often severe, and sometimes life-threatening or fatal side effects. One of the most serious is VLS, which can affect the entire body and virtually every body system, organ, or tissue.

According to the "package insert" provided by Chiron Therapeutics, IL-2 (PROLEUKIN®) is a highly purified protein with a molecular weight of approximately 15,300 Daltons. The chemical name is des-alanyl-1, serine-125 human interleukin-2. IL-2, a lymphokine, is produced by recombinant DNA technology using a genetically engineered E. coli strain containing an analogue of the human interleukin-2 gene. Genetic engineering techniques were used to modify the human IL-2 gene, and the resulting expression clone encodes a modified human interleukin-2. This recombinant form differs from the native interleukin-2 in the follow ways: a) IL-2 is not glycosylated because it is derived from E. coli; b) the molecule has no N-terminal alanine; the codon for this amino acid was deleted during the genetic engineering procedure; c) the molecule has serine substituted for cysteine at amino acid position 125; this was accomplished by site specific manipulation during the genetic engineering procedure; and d) the aggregation state of PROLEUKIN® is likely to be different from that of native interleukin-2.

In addition, Chiron Therapeutics indicates that certain in vitro studies were performed to determine the properties of PROLEUKIN® and that these include: a) enhancement of lymphocyte mitogenesis and stimulation of long-term growth of human interleukin-2 dependent cell lines; b) enhancement of lymphocyte cytotoxicity; c) induction of killer cell (lymphokine-activated [LAK] and natural [NK] activity; and d) induction of interferon-gamma production. In in vivo studies, IL-2 produces multiple immunological effects in murine models in a dose-dependent manner. These include: a) activation of cellular immunity with profound lymphocytosis, eosinophilia, and thrombocytopenia; b) the production of other cytokines such as tumor necrosis factor, interleukin-1, and gamma interferon; c) inhibition of tumor growth. In addition, as noted previously, interleukin-2 has now been shown to stimulate the production of potentially toxic and inflammatory leukotriene $B_4$. Despite the large amount of knowledge concerning the effects of IL-2, the exact mechanism by which IL-2 mediates its antitumor (and toxic) effects in humans is unknown.

A compound useful in this invention is administered to an appropriate subject in need of these compounds by a medically acceptable route of administration such as orally, parenterally (e.g., intramuscularly, intravenously, subcutaneously, interperitoneally), transdermally, rectally, by inhalation and the like.

Unit doses or multiple dose forms are contemplated, each offering advantages in certain clinical settings. The unit dose would contain a predetermined quantity of active compound calculated to produce the desired effect(s) in the setting of IL-2 coadministration. The multiple dose form may be particularly useful when multiples of single doses, or fractional doses, are required to achieve the desired ends. Either of these dosing forms may have specifications that are dictated by or directly dependent upon the unique characteristic of the particular compound, the particular therapeutic effect to be achieved (e.g., the attenuation of IL-2 toxicity, especially VLS), and any limitations inherent in the art of preparing the particular compound for treatment of IL-2 toxicity or VLS in living subjects.

A unit dose will contain an amount sufficient to mitigate the adverse effects induced by excess IL-2 in a subject and may contain from about 5.0 to 1000 mg of compound with the preferred range being 50 to 350 mg. The multiple dose form could contain from 0.2 to 4,000 mg with the preferred range being 100 to 600 mg.

The compound will preferably be administered orally in a suitable formulation as an ingestible tablet, a buccal tablet, capsule, caplet, elixir, suspension, syrup, trouche, wafer, lozenge, and the like. Generally, the most straightforward formulation is a tablet or capsule (individually or collectively designated as an "oral dosage unit"). Suitable formulations are prepared in accordance with a standard formulating techniques available that match the characteristics of the compound to the excipients available for formulating an appropriate composition. A tablet or capsule will contain about 25 to about 500 mg of a compound of Formula (I), preferably about 50–250 mg, and most preferably about 100–200 mg.

The form may deliver the LA rapidly or may be a sustained-release preparation. The LA may be enclosed in a hard or soft capsule, may be compressed into tablets, or may be incorporated with beverages, food or otherwise into the diet. The percentage of the final composition and the preparations may, of course, be varied and may conveniently range between 1 and 70% of the weight of the final form, e.g., tablet. The amount of LA in such therapeutically useful compositions is such that a suitable dosage will be obtained. Preferred compositions according to the current invention are prepared so that an oral dosage unit form contains between about 2.5 to about 50 LA by weight (%w) in dosage units weighing between 50 and 1000 mg.

The suitable formulation of an oral dosage unit may also contain: a binder, such as gum tragacanth, acacia, corn starch, gelatin; sweetening agents such as lactose or sucrose; disintegrating agents such as corn starch, alginic acid and the like; a lubricant. such as magnesium stearate; or flavoring such a peppermint, oil of wintergreen or the like. Various other material may be present as coating or to otherwise modify the physical form of the oral dosage unit. The oral dosage unit may be coated with shellac, a sugar or both. Syrup or elixir may contain the LA, sucrose as a sweetening agent, methyl and propylparabens as a preservative, a dye and flavoring. Any material utilized should be pharmaceutically-acceptable and substantially non-toxic. Details of the types of excipients useful may be found in the nineteenth edition of "Remington: The Science and Practice of Pharmacy," Mack Printing Company, Easton, Pa. See particularly chapters 91–93 for a fuller discussion.

A compound may be administered parenterally, e.g., intravenously, intramuscularly, intravenously, subcutaneously, or interperitoneally. The carrier or excipient or excipient mixture can be a solvent or a dispersive medium containing, for example, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Except in so far as any conventional media or agent is incompatible with the active ingredient, use in therapeutic compositions is contemplated. Moreover, other or supplementary active ingredients can also be incorporated into the final composition. The dosage of the parenteral dosage unit will be 0.1–100% of the oral dosage unit, preferably 10–100%, more preferably 30–100%, and most preferably 50–100%.

Solutions of the LA may be prepared in suitable diluents such as water, ethanol, glycerol, liquid polyethylene glycol (s), various oils, and/or mixtures thereof, and others known to those skilled in the art.

The pharmaceutical forms suitable for injectable use include sterile solutions, dispersions, emulsions, and sterile powders. The final form must be stable under conditions of manufacture and storage. Furthermore, the final pharmaceutical form must be protected against contamination and must, therefore, be able to inhibit the growth of microorganisms such as bacteria or fungi. A single intravenous or intraperitoneal dose can be administered. Alternatively, a slow long term infusion or multiple short term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

In all cases involving an injectable product the final form, as noted, must be sterile and must also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Prevention or inhibition of growth of microorganisms may be achieved through the addition of one or more antimicrobial agents such as chlorobutanol, ascorbic acid, parabens, thermerosal, or the like. It may also be preferable to include agents that alter the tonicity such as sugars or salts.

Another aspect of this invention is an article of manufacture that comprises a pharmaceutical composition comprising a leukotriene $B_4$ antagonist, preferably a leukotriene $B_4$ receptor antagonist (as described herein), as a unit dosage in combination with printed labeling instructions for administering the composition to a mammal undergoing treatment of a malignancy or viral disease with IL-2, wherein the amount of the composition administered is sufficient to reduce IL-induced adverse pharmacological effects in the mammal being treated.

There are several advantages of this invention. It reduces or obviates the need to place patients into intensive care units and onto respirators in the case of severe pulmonary edema, or to place patients into cardiac or coronary care units in the case of severe arrhythmias or congestive heart failure or onto dialysis protocols in the case of renal compromise. It reduces intensive nursing care or supportive care or need of ICUs or CCUs. The mitigation of IL-2-related adverse events enables the safe administration of higher doses of IL-2 such that the antitumor efficacy of the combined regimen (LA+IL-2) is superior to IL-2 alone. It reduces diagnostic testing required to monitor patient responses to IL-2 and to determine the success of therapeutic interventions required to mitigate IL-2-related adverse events. It reduces diagnostic testing needed to demonstrate that certain events are caused by IL-2 rather than by another agent. It reduces the costs associated with diagnosing or treating IL-2-induced adverse events, particularly those associated with VLS. Another advantage of this invention is that it preserves or enhances the activity of IL-2 (or, at a minimum, reduces the adverse effects of IL-2 more than any reduction in activity of IL-2). A further advantage is that it permits the administration of higher and more effective doses of IL-2 without increasing the risk of adverse effects from IL-2, especially VLS.

It can be seen from the foregoing discussion that my invention improves the benefit to risk ratio and can be said to improve the therapeutic index. Therapeutic index, in its most general form, relates the benefits derived from a particular treatment or therapy to the risks associated with that same treatment or therapy. Somewhat more mathematically, the therapeutic index may be calculated as the dose or dose level of a drug that provides useful clinical benefit as compared to the dose or dose level of the same drug that causes adverse events of such severity that the adverse-event causing dose is not tolerated. The ratio of these two doses or dose-levels has been described as the "therapeutic index." Still a third useful definition is the ratio of the change in an objective benefit to the change in an objective risk caused by some type of intervention during therapy. The intervention could be the administration of another drug or drugs or the performance of a medical or surgical procedure, or a combination of these. Those skilled in the art will recognize that other definitions may exist which, nevertheless, connote the fundamental concepts described herein.

Most simply, a therapeutic index changes if the benefits change but the risks do not, or the risks change but the benefits do not. However, it is possible that risks and benefits may change simultaneously, in the same or opposite directions and with similar or different magnitudes. Then the direction and relative magnitude of the changes become determinant regarding the effect on the therapeutic index.

The possible changes in risks and benefits and the effect on therapeutic index are shown in the table below.

TABLE 1

Effect of an Intervention on Benefits, Risks, and Therapeutic Index

| Change in Benefits | Change in Risks | Therapeutic Index |
|---|---|---|
| increase | no change | increase |
| increase | decrease | increase |
| no change | increase | decrease |
| decrease | no change | decrease |
| decrease | increase | decrease |
| no change | decrease | increase |
| increase | increase (less than increase in change in benefits) | increase |
| increase | increase (more than increase in change in benefits) | decrease |
| decrease | decrease (less than decrease in change in benefits) | decrease |
| decrease | decrease (more than decrease in change in benefits) | increase |

Note, however, that in order to determine the effect on therapeutic index of any intervention that effects either risks or benefits it is essential to determine the changes in direction and magnitude of both risks and benefits. No useful statement regarding the impact of an intervention on therapeutic index can be made without knowing simultaneously the effects on risks and benefits.

All medical judgments regarding the utility of a particular therapeutic or medical or surgical intervention are made on the basis of the therapeutic or interventional impact on the therapeutic index. This reliance on therapeutic index may be explicit or implicit but it is invariant in medical decision-making. I have found that the use of $LTB_4$ antagonist (particularly a $LTB_4$ receptor antagonist) will improve the therapeutic ratio of IL-2 treatment by increasing the benefits of treatment while decreasing the risks.

Figure 1:
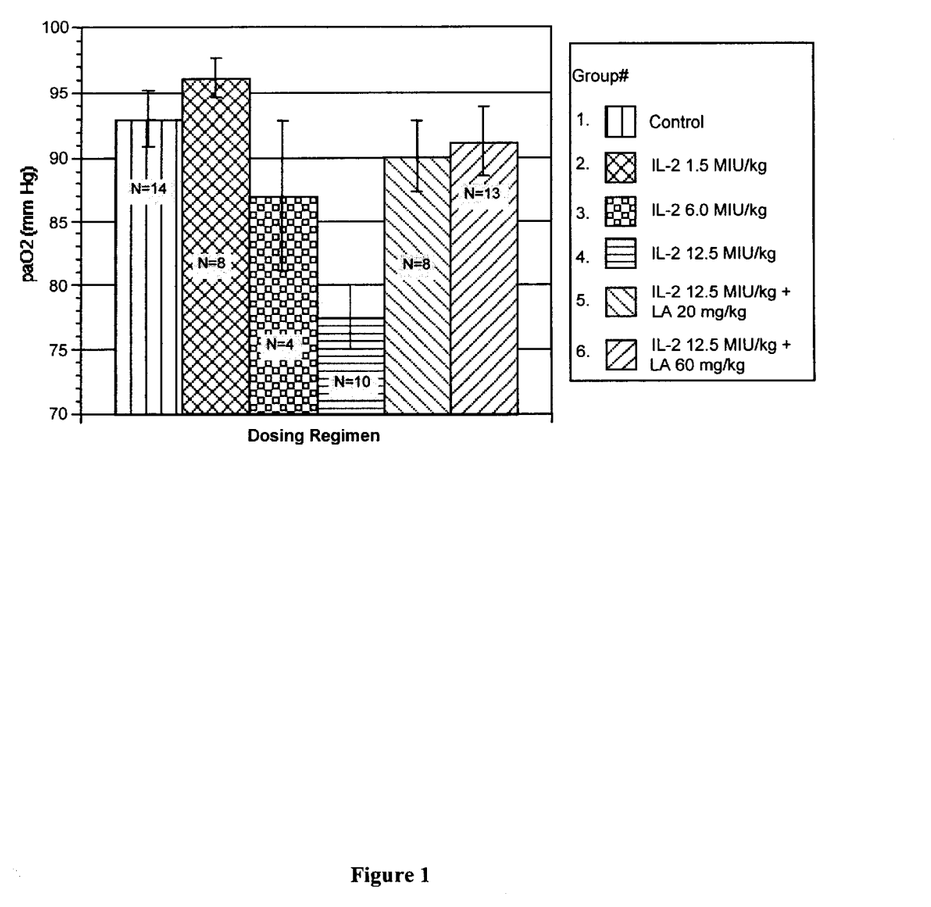
FIG. 1: This figure presents comparative in vivo results showing the effects of a compound useful in this invention on the reduction of oxygenation of arterial blood by IL-2 administration.
Figure 2:
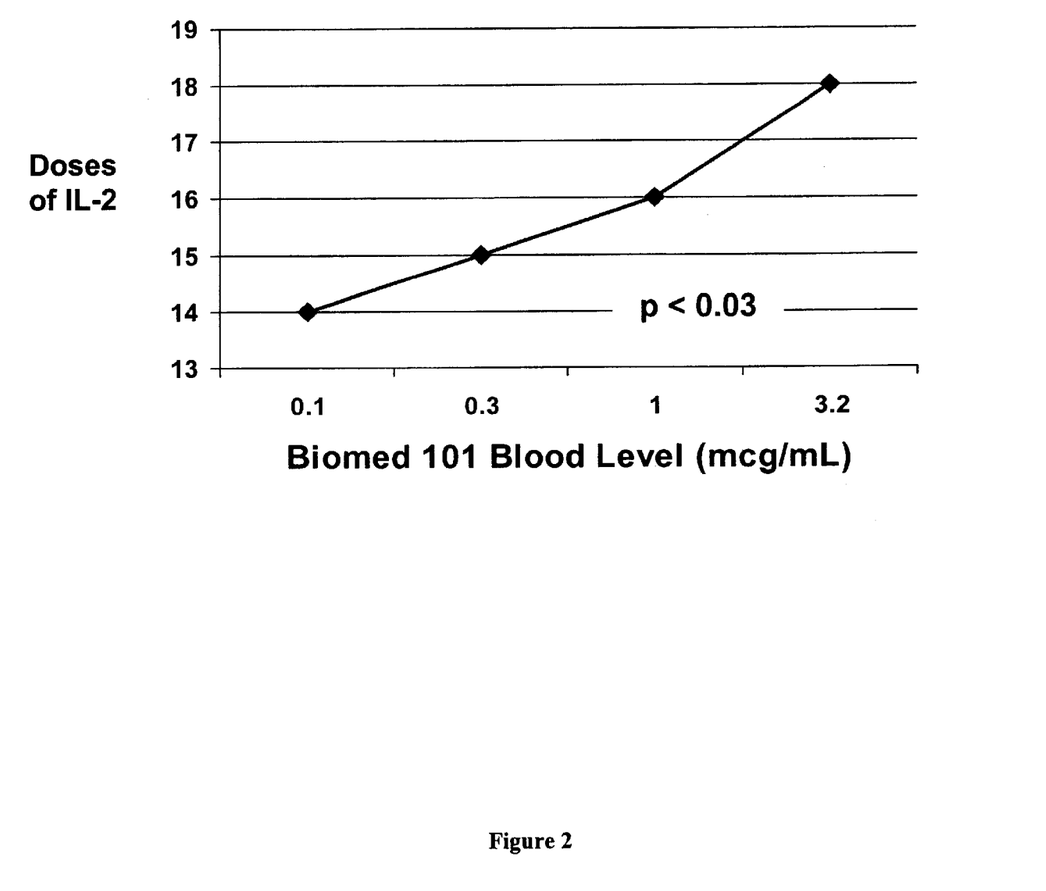
FIG. 2: This figure presents the number of doses of IL-2 that could be safely administered to patients with metastatic renal cell cancer as related to the plasma level of a leukotriene $B_4$ antagonist useful in this invention. As leukotriene $B_4$ antagonist plasma level rises, the number of well-tolerated doses of IL-2 also increases ($p<0.03$).

The effect of an LTB4 receptor antagonist to decrease the risks associated from IL-2 exposure may be seen in FIG. 1. As shown, when compared to control values, oxygen levels in the blood decline when IL-2 alone is given but do not decline appreciably when IL-2 is co-administered with an LTB4 receptor blocker. Thus, the risks of IL-2 have been reduced.

The effect of an LTB4 receptor blocker to increase the benefits associated with IL-2 exposure may be seen in Table 4 (in Example 5). As shown, the number of pulmonary metastases are fewer when IL-2 is co-administered with an LTB4 receptor blocker than when IL-2 is administered alone. Thus, the benefits of IL-2 have been preserved or enhanced.

Expressed more quantitatively, then, the impact on the risks and benefits of utilizing IL-2 with or without an LTB4 antagonist may be calculated by comparing the change in the number of metastases (benefit) to the change in blood oxygen (risk) when the treated groups are compared with the control (untreated) group. The therapeutic index in this setting is expressed as a ratio of the change in number (N) of metastases to change in blood oxygenation (mm Hg) and expressed in units of "N/mm Hg."

These calculations are shown in the table below:

TABLE 2

| Treatment | Changes in Metastases (mean) (N) | Change in Oxygen (mean) (mm Hg) | Therapeutic Index (N/mm Hg) |
|---|---|---|---|
| IL-2 alone | −32 | −15 | 2.1 |
| IL-2 + LTB4 antagonist | −42 | −2 | 21.0 |

Thus, it may be observed that the therapeutic index is much improved, both qualitatively and quantitatively, when IL-2 is used in conjunction with the $LTB_4$ antagonist than when IL-2 is utilized alone. This is the first practical demonstration of an improvement in therapeutic index of combination therapy with IL-2.

A compound of particular value in this invention is (±)7-[3-(4-acetyl-3-methoxy-2-propylphenoxy)propoxy]-3,4-dihydro-8-propyl-2H-1-benzopyran-2-carboxylic acid. The compound is a potent, highly selective leukotriene $B_4$ receptor antagonist. A summary of its properties appears below.

In Vitro Pharmacology

Inhibition of $LTB_4$ binding to human neutrophils
IC50=0.3 micromolar
Inhibition of $LTB_4$ chemotaxis
range=0.3–3.0 micromolar
Inhibition of human neutrophil adhesion to $LTB_4$-stimulated umbilical vein endothelial cells
range=0.3–1.0 micromolar
Inhibition of $LTB_4$-induced neutrophil granulation
range=1–3 micromolar
Inhibition of $LTB_4$ synthesis
IC50=2.1 micromolar
Inhibition of $LTA_4$ conversion into $LTB_4$
IC50=20 micromolar In Vivo Pharmacology Inhibition of $LTB_4$ chemotaxis in guinea pigs
ED50=0.6 mg/kg i.g.
Inhibition of 12 (R)-HETE in guinea pigs
ED50=20 mg/kg i.g.
Inhibition of acetic acid colonic inflammation in rats and guinea pig ED50=20 mg/kg i.g.

Inhibition of calcium ionophore dermal inflammation in the guinea pig ear

ED50=0.7 mg/ear

These in vitro and in vivo data establish the potency and selectivity of the preferred compound and are particularly relevant to diminishing, i.e., mitigating the unwanted effects of IL-2. These data are also particularly relevant to establishing that leukotriene $B_4$ mediated responses, including VLS, whether induced initially by administration of IL-2 or by other means, are blunted by the preferred compound.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

EXAMPLE 1

This example is a reproduction (without formulae) of Example 1 from U.S. Pat. No. 4,889,871 and sets forth a method for making a preferred compound useful in this invention, 7-[3-(4-acetyl-3-methoxy-2-propylphenoxy) propoxy]-3,4-dihydro-8-propyl-2H-1-benzopyran-2-carboxylic acid.

(a) 493 mg of methyl 7-[3-(4-acetyl-3-hydroxy-2-propylphenoxy)propoxy]-3,4-dihydro-8-propyl-2H-1-benzopyran-2-carboxylate was added to 25 ml of acetone containing 276 mg of anhydrous potassium carbonate and 282 mg of methyl iodide. The mixture was refluxed for about 24 hours and water was added and the mixture was then extracted with ethyl acetate. The extract was dried, the solvent removed under vacuum, and the residual oil was chromatographed over silica gel with a 40/60 mixture of ethyl acetate/hexane to provide pure-methyl ether, methyl 7-[3[(4-acetyl-3-methoxy-2-propylphenoxy)propoxy]-3,4-dihydro-8-propy-2H-1-benzopyran-2-carboxylate.

(b) The methyl ether (340 mg) was dissolved in methanol (5 ml) containing lithium hydroxide (0.7 ml of a 2N LiOH solution in water). The mixture was stirred at room temperature overnight and the solvent removed in vacuo. The residue was partitioned between ethyl acetate and 2N HCl and the organic layer separated and washed with brine. Evaporation of the volatiles in vacuo afforded crude acid. This material was purified by silica gel chromatography using ethyl acetate/hexane/acetic acid (40:60:0.5) as eluant. The pure product was recrystallized from ethyl acetate/hexane to afford 200 mg of product, 7-[3-(4-acetyl-3-methoxy-2-propylphenoxy)propoxy]-3,4-dihydro-8-propyl-2H-1-benzopyran-2-carboxylic acid, m.p. 65°–68° C.

Microanalysis: Found: C, 69.22; H, 7.53. Theory: C 69.40, H 7.49.

The NMR (CDCl$_3$) shows a —OCH$_3$ at δ3.75.

EXAMPLE 2

This example explains how compound of Formula (I) is administered to sheep to mitigate the adverse effect of excess IL-2.

Preparation of Sheep

Yearling male or female interbred sheep (N Å 24) and weighing approximately 20 to 40 kg are prepared with chronic lung lymph fistulae essentially according to a modification of the technique described by Staub et al (see "Relevant Literature," supra at 6 and as further described within reference 2 herein and other references cited within reference 2). Through a thoracotomy, the efferent duct of the caudal mediastinal lymph node is cannulated, the distal portion of the lymph node below the level of the inferior pulmonary ligament is ligated, and the diaphragm around the lymph node is circumferentially cauterized or otherwise securely closed. All visible systemic lymph tributaries to the proximal portion are cauterized or ligated to minimize extra-pulmonary contamination of collected lymph. A suitable thermistor-tipped pulmonary arterial and central venous catheter are introduced through the right internal jugular vein. The aorta is then cannulated via the adjacent carotid artery. After a recovery period of a variable number of days, preferably 4–5, when the animals appear vigorous again, are afebrile, and have a steady flow of blood-free lymph, the experiment is conducted.

Measurement of Cardiopulmonary Function

To measure cardiopulmonary function, suitable strain-gauge transducers are used to measure the following pressures: mean arterial pressure (MAP); mean pulmonary wedge pressure (MPAP, and the pulmonary arterial wedge pressure (PAWP). The pulmonary microvascular pressure (Pmv) is calculated from the Gaar equation where Pmv=PAWP+0.4 ¥ (MPAP-PAWP). Pulse rate is determined from the arterial pressure tracings. Cardiac output is measured serially by thermodilution or dye techniques using suitable, standard equipment. Arterial blood gases, pH, oxygen saturation, and hemoglobin levels are also measured with suitable, standard laboratory equipment and by spectrophotometry using extinction coefficients determined for the species being tested.

Hematology

Circulating platelets and leukocytes are counted by means of standard laboratory equipment or by phase microscopy while leukocyte differential counts are determined by counting microscopically on ruled stages of Wright's stained blood smears.

Biochemical Assays

Concentrations of leukotriene $B_4$ and thromboxanes are measured using standard radioimmunoassays. Such measurements are or can be made on lung lymph as well. In addition, lymphatic (LY) and plasma (PL) total protein concentrations are determined by using standard spectrophotometric techniques. The LY/PL protein ratio is calculated and multiplied by lymph flow (QL) to obtain the lymphatic protein clearance rate.

IL-2

The recombinant interleukin-2 (PROLEUKIN®) is utilized. The dose of IL-2 can be varied as desired. The preferred range is 1,000 to 1,000,000 IU/kg while the most preferred range is 400,000 to 800,000 IU/kg.

Protocol

Experiments are or can be performed on conscious, instrumented sheep having free access to food and water. Sheep are allowed to stand or recline as desired. Transducers are re-leveled as necessary to accommodate the sheep stance or posture. Baseline measurements are obtained for variable lengths of time with the preferred period being at least one hour.

Certain animals receive IL-2 alone, 400,000 to 800,000 IU/kg, given either as a bolus injection over one to several minutes or as a slower infusion over several minutes to several hours. Other animals receive the same IL-2 treatment but also receive, for example, the compound. The compound may be given by any of the routes identified previously. For simplicity in the animal laboratory, intravenous dosing is preferred although oral dosing is also acceptable. Effective doses of the LA range from 0.1 mg/kg/day to 10 mg/kg/day, while the preferred dose range is 0.1 to 2.0 mg/kg/day and the most preferred dose range is 0.5 to 1.0 mg/kg/day. When given intravenously, the LA may be dosed either as a bolus injection over one to several minutes or as a slower infusion over several minutes to several hours. Maintaining continuous but not necessarily invariant levels of LA during IL-2 exposure is preferred but is not necessary. LA dosing may begin before, during, or after the IL-2 administration. It is preferred to begin LA before IL-2 administration and is most preferred to begin dosing at least one hour prior to the start of IL-2 administration. The purpose of this prophylactic regimen is to establish effective blockade of the leukotriene $B_4$ receptors prior to IL-2-induced increases in plasma levels of leukotriene $B_4$.

Cardiopulmonary function, lymph flows and protein content, hematology and other chemical laboratory tests are assessed during and for several hours after IL-2 administration begins. In this model it is preferred to monitor animals as described for a period of 4–6 hours.

Results

The in vitro and in vivo results demonstrate the effectiveness of the referenced compound in mitigating, reducing or eliminating leukotriene $B_4$ induced biological responses. Appropriate analysis of the data from the ovine experiment described herein extend the beneficial effects of LA's, LA's preferably, and the referenced LA most preferably, to the setting of preventing IL-2-induced VLS and adverse alterations in cardiopulmonary function and laboratory testing.

EXAMPLE 3

This example explains how a compound of Formula (I) is administered to rats to mitigate the adverse effect of excess IL-2 in rats.

Test Material

A preferred LA compound, (±) 7-[3-(4-acetyl-3-methoxy-2-propylphenoxy)propoxy]-3,4-dihydro-8-propyl-2H-1-benzopyran-2-carboxylic acid, (Lot Number 101-8802) was supplied as a white crystalline solid by BioMedicines, Inc. For intraperitoneal (i.p.) injection, the LA was freshly dissolved in a mixture of 0.1 M potassium phosphate buffer (pH 6.8), ethanol, and propylene glycol (65:20:15 by volume). The concentration of the LA solution was adjusted so that the volume for each injection was 3 ml/kg for all groups.

Proleukin® for Injection (Chiron Therapeutics) recombinant human interleukin-2 (IL-2), is supplied as a lyophilized powder in vials containing 22 million international units (MIU). For intravenous (i.v.) injection, Proleukin was reconstituted with Sterile Water for Injection, USP, to provide a solution of 18 million IU/ml. The reconstituted solution was further diluted with 5% Dextrose Injection, USP as needed so that the volume for each injection was 0.208 ml/rat. The dose can be varied as usual. The preferred range for purposes of this example is 6–24 MIU/kg while the most preferred range is 10–15 MIU/kg. Any of the previously mentioned routes of administration may be used. The preferred route is i.v. or intraperitoneal (i.p.) while the most preferred, for purposes of this example, is i.v.

Animals

Male Sprague Dawley rats were obtained from Harlan Sprague Dawley, Inc., Indianapolis, Ind. All rats were six to eight weeks old and weighed approximately 250 to 300 g when used in the experiments. Each animal was numbered on the tail with indelible ink. The animals were housed in groups of up to three per cage and were allowed access to standard chow and water ad libitum. The study was conducted at an AAALAC accredited facility in compliance with the National Institutes of Health "Guide for the Care and Use of Laboratory Animals," Publication No. 86-23 and the USDA Laboratory Animal Welfare Act, Publication L. 89-544.

Experimental Protocol

Six groups of animals were studied (total N=57) in a modification of the technique of Edwards et al (Edwards M J, Miller F N, Simms D E et al. Interleukin-2 Acutely Induces Platelet and neutrophil-Endothelial Adherence and Macromolecular Leakage. Cancer Research 52: 1992:3425–31). Animals were weighed on the day of dosing and the appropriate doses of IL-2 and/or LA were calculated. The animals remained conscious throughout the experiment until an anesthetic was administered approximately 10 minutes before exsanguination. The anesthetic consisted of a mixture of ketamine (45 mg/ml) xylazine (2.5 mg/ml), and acepromazine (0.37 mg/ml) diluted with water and administered subcutaneously at a dose of 2.0 ml/kg.

Group 1 (n=14) consisted of control animals that received both i.v. and i.p. injections of vehicle. The other five groups received i.v. injections of IL-2 via the tail vein. Groups 2 (n=8), 3 (n=4), and 4 (n=10) received IL-2 in doses of 1.5, 6.0, and 12.5 million IU(MIU)/kg, respectively. In addition to 12.5 million IU/kg of IL-2, Groups 5 (n=8) and 6 (n=13) received i.p. injections of the LA. The LA was administered in two equal, divided doses; the first dose of LA was given 20 minutes before administration of IL-2 and the second dose was given 50 minutes after administration of IL-2. Group 5 was administered 2×10 mg/kg of the LA. Group 6 was administered 2×30 mg/kg of the LA.

Two hours after the IL-2 injection, the animals were exsanguinated via the abdominal aorta and the arterial blood was collected for measurement of PaO2.

Measurement of Blood Oxygen Levels

Whole arterial blood was collected into heparinized blood arterial gas syringes. Immediately after collection, the blood sample was analyzed using PaO2 electrode model DO-166FT. Sample blood was pre-oxygenated and used as a standard before and after each test sample.

Analysis of Data

Data are shown as mean±SEM. Data were analyzed using the Tukey-Kramer test (JMP® statistical software from SAS, Inc.) Significance was defined as a p-value less than 0.05.

Results of In vivo Study

Progressively higher doses of interleukin-2 progressively reduced arterial oxygen levels in the rodent. With a dose of 12.5 MIU IL-2, oxygen levels in the rat declined from a control value of 93.0±2.2 mm Hg to 77.5±2.5 mm Hg (p<0.001). When LA was administered as described the reduction in oxygenation induced by IL-2 was mitigated (p>0.5 vs control and p<0.001 vs IL-2 alone for both LA-treated groups; see FIG. 1).

Discussion

Interleukin-2 predictably lowers arterial oxygenation in humans when administered in a sufficiently high dose. This is an adverse pharmacological effect. This reduction in oxygenation is attributable to impaired ventilatory responses that occur, at least in part, because of the VLS induced by IL-2. The current in vitro findings demonstrate that the LA utilized in this example blocks leukotriene $B_4$ receptors and thereby reduces leukotriene $B_4$ activity. Furthermore, the in vivo findings demonstrate that the administration of an LA prevents the clinically important adverse event of hypoxemia associated with exposure to IL-2 and thereby demonstrating a beneficial effect in preventing the VLS caused by IL-2.

EXAMPLE 4

This example shows that the specific leukotriene $B_4$ ($LTB_4$) antagonist used in Example 3 (referred to here as "BioMed 101")could prevent VLS in a rat model of IL-2-induced toxicity.

Materials and Methods

Animals

Male Sprague Dawley rats were obtained from Harlan Sprague Dawley, Inc., Indianapolis, Ind. All rats were six to eight weeks old and weighed approximately 250 to 300 g when used in the experiments. The study was conducted at an AAALAC accredited facility in compliance with the National Institutes of Health "Guide for the Care and Use of Laboratory Animals," Publication No. 86-23, and the USDA Laboratory Animal Welfare Act, Publication L. 89-544.

Test Materials

Proleukin® for Injection (Chiron Therapeutics) recombinant human IL-2 was purchased from a commercial retail supplier. Proleukin is supplied as a lyophilized powder in vials containing 22 million international units (IU). For intravenous (i.v.) injection, Proleukin was reconstituted with Sterile Water-for-Injection, USP, to provide a solution of 18 million IU/ml. The reconstituted solution was further diluted with 5% Dextrose Injection USP as needed so that the volume for each injection was 0.208 ml/animal. Vehicle for IL-2 was prepared in a similar manner.

Biomed 101 was supplied as a white crystalline solid by BioMedicines, Inc. (Alameda, Calif.). For purposes of subsequent intraperitoneal injection, Biomed 101 was freshly dissolved in a mixture of 0.1 M potassium phosphate buffer (pH 6.8), ethanol, and propylene glycol (65:20:15 by volume). The concentration of the Biomed 101 solution was adjusted so that the volume for each injection was 3 ml/kg for all groups. The Biomed 101 vehicle was prepared in a similar manner with adjustments made to equalize the volume of injectate.

Experimental Protocol

Six groups of animals were studied (total N=59). Animals were weighed on the day of dosing and the appropriate doses of IL-2 and/or Biomed 101 were calculated. The animals remained conscious throughout the experiment until an anesthetic was administered approximately 10 minutes before planned exsanguination. The anesthetic consisted of a mixture of ketamine (45 mg/ml), xylazine (2.5 mg/ml), and acepromazine (0.37 mg/ml) diluted with water and administered subcutaneously at a dose of 2.0 ml/kg.

IL-2 or IL-2 vehicle was administered by bolus injection via the tail vein. Biomed 101 or Biomed 101 vehicle was administered by intraperitoneal injection. Biomed 101 or the related vehicle was administered in two equal doses, the first dose given 20 minutes before administration of IL-2 and the second dose given 50 minutes after administration of IL-2. Two hours after the injection of IL-2 or IL-2 vehicle, animals were exsanguinated via the abdominal aorta and the arterial blood was collected for measurement of $PaO_2$.

Group 1 (n=13) consisted of control animals that received injections of each vehicle, either i.v. or i.p. as appropriate. The other five groups received i.v. bolus injections of IL-2 via the tail vein. Groups 2 (n=8), 3 (n=5), and 4 (n=13) received IL-2 in doses of 1.5, 6.0, and 12.5 million IU/kg, respectively. In addition to 12.5 million IU/kg of IL-2, Groups 5 and 6 also received i.p. injections of Biomed 101 both prophylactically and following IL-2 administration as noted above. Group 5 (n=12) received two doses of 30 mg/kg of Biomed 101 (total=60 mg/kg). Group 6 (n=8) received two doses of 10 mg/kg of Biomed 101 (total=20 mg/kg).

The study was conducted in two phases. In the first phase of the study, animals were treated with rising doses of IL-2 to determine a dose of IL-2 that could significantly lower $PaO_2$. Dosing was completed in Group 1, Group 2, Group 3 and in five animals in Group 4 before any animals received Biomed 101. Subsequently, to further control for potential variability in response, at least two animals were dosed in Group 4 (IL-2 12.5 MIU/kg alone) on each day that animals were dosed in Groups 5 and 6 (IL-2 12.5 MIU/kg plus one of the two doses of Biomed 101).

Measurement of Blood Oxygen

Whole arterial blood was collected into heparinized syringes. Immediately after collection, the blood sample was analyzed using a Lazar Research Laboratories flow-through dissolved-oxygen probe. The cell temperature was set to 37 degrees centigrade. A syringe pump was set to 0.5 ml/min to introduce the sample. The cell was zeroed using a solution of heparin and isotonic saline equilibrated with 100% nitrogen. The cell was then calibrated using a solution of heparin and isotonic saline equilibrated with 20% oxygen. After each $PaO_2$ determination in whole blood was made, the cell was washed with heparin ad isotonic saline. A 20% $O_2$ standard was introduced before each sample to ensure accurate and reliable measurements.

Measurement of Biomed 101 Plasma Levels

In animals dosed with Biomed 101, plasma levels of Biomed 101 were assayed with a validated, high-pressure liquid chromatographic method.

Statistical Analysis

In previously published studies, IL-2 administration in the rat resulted in average decreases of $PaO_2$ from approximately 92 mm Hg to 79 mm Hg (with an average standard deviation of approximately 6 mm Hg). We calculated that studying five animals per group would give approximately an 85% power to detect such a difference at a two-sided p-value of 0.05. Sample sizes of 13 animals per group would be necessary to have an 80% power to detect a difference between 79 mm Hg in the interleukin-only treatment group and 86 mm Hg in the interleukin plus Biomed 101 treatment group with a two-sided p-value of 0.05 assuming standard deviations of 6 mm Hg in each group.

The primary comparison of interest was the difference between the average $PaO_2$s in the interleukin-only treatment group and the group(s) treated with Biomed 101. If the data appeared to be normally distributed, the comparison was to be made using Student's t-test. If inspection of the data indicated that assumptions of the Student's t-test were not applicable, a non-parametric test would be used.

A p-value of 0.05 was to be considered statistically significant. If the mean $PaO_2$ in the first Biomed 101-treated group was significantly higher than the value in the IL-2 only group, it was then planned to decrease the dose of Biomed 101 in the next group of animals; otherwise it was planned to increase the dose of Biomed 101 in the next group.

Because only two primary comparisons of interest were planned, it was not considered necessary to adjust p-values for multiple comparisons.

Results

The average PaO2 in animals receiving only the two vehicles was 93.0±2.2 mm Hg (mean±the standard error of the mean). Administration of Proleukin® IL-2 at a dose of 1.5 million IU/kg resulted in no observable acute effect on $PaO_2$. Administration of 6 million IU/kg of IL-2 resulted in decreases in $PaO_2$ in some of the animals. Evaluation of the data after five animals had been dosed with 12.5 MIU/kg suggested that the mean $PaO_2$ decreased significantly and approximately 1.8 mm Hg for each increase of 1 MIU/kg in IL-2 administered, as shown in FIG. 1. Therefore, the IL-2 dose of 12.5 MIU/kg was chosen for the IL-2 comparison group and the same dose of IL-2 was administered to animals that also received Biomed 101.

Mean and median $PaO_2$ values in animals dosed with 12.5 MIU/kg alone or with Biomed 101 are summarized in the table below. As noted, 12.5 MIU/kg IL-2 alone produced a significant fall in $PaO_2$. Median $PaO_2$ was significantly higher, however, in animals also dosed with Biomed 101 and not significantly different than the value observed in control animals.

The mean plasma level (±the standard error of the mean) of Biomed 101 associated with these effects on oxygenation was 6.4 (±0.89) μg/ml in the group of animals dosed with 60 mg/kg Biomed 101 and was 2.0 (±0.26) μg/ml in the group of animals dosed with 20 mg/kg Biomed 101.

Discussion

This example directly evaluated the effect of leukotriene $B_4$ ($LTB_4$) receptor blockade on the toxicity associated with IL-2 administration. Based on the results of this example, blockade of the $LTB_4$ receptor with Biomed 101 appears to mitigate IL-2 vascular toxicity in the rodent as judged by the absence of hypoxemia after high-dose IL-2. Co-administration of Biomed 101 and IL-2 was shown to prevent the marked reduction in blood oxygen levels caused by administration of IL-2 alone.

EXAMPLE 5

The primary objective of this Example was to determine whether co-administration of Biomed 101 with IL-2 would affect the anti-tumor activity of IL-2 in a well-studied murine model of B16 melanoma lung metastases.

Materials and Methods

Animals

Female C57BL/6 mice were obtained from Charles River, Raleigh.

Test Materials

Proleukin® for Injection (Chiron Therapeutics) recombinant human IL-2 was purchased from a commercial retail supplier. Proleukin is supplied as a lyophilized powder in vials containing 22 million international units (IU). For intravenous (i.v.) injection, Proleukin was reconstituted with Sterile Water-for-Injection, USP, to provide a solution of 18 million IU/ml. The reconstituted solution was further diluted with 5% Dextrose Injection USP as needed so that the volume for each injection was 0.1 mL/10 g body weight. Vehicle for IL-2 was prepared in a similar manner.

For this Example, Biomed 101 was supplied as a white crystalline solid by BioMedicines, Inc (Alameda, Calif.). For purposes of subsequent intraperitoneal injection, Biomed 101 was freshly dissolved in a mixture of 0.1 M potassium phosphate buffer (pH 6.5), ethanol, and propylene glycol (65:20:15 by volume). The concentration of the Biomed 101 solution was adjusted so that the volume for each injection was 0.1 mL/10 g body weight. The Biomed 101 vehicle was prepared in a similar manner with adjustments made to equalize the volume of injectate. The intraperitoneal dose of 25 mg/kg bid for 4 days was shown in a preliminary study to be the highest tolerated dose of Biomed 101 in tumored mice treated with IL-2.[22]

The B16/BL6 murine melanoma tumor cells for injection were obtained from in vitro culture. Mice were inoculated with $3 \times 10^5$ cells intravenously on Day 0.

Experimental Protocol

Three groups of animals received test articles as per protocol summarized in Table 1 below.

TABLE 3

Schedule of Treatments

| Group # (N) | Test Articles | Dosage (mg/kg/ dose) | Route | Schedule |
|---|---|---|---|---|
| Group 1 (20) | IL-2 vehicle | | iv | q6hx2, qdx4, 15 min |
| | Biomed 101 vehicle | | ip | q6hx2, qdx4, 0 min |
| Group 2 (20) | IL-2 | 1 mg/kg | iv | q6hx2, qdx4, 15 min |
| | Biomed 101 vehicle | | ip | q6hx2, qdx4, 0 min |
| Group 3 (20) | IL-2 | 1 mg/kg | iv | q6hx2, qdx4, 15 min |
| | Biomed 101 | 25 mg/kg | ip | q6hx2, qdx4, 0 min |

Tumor cells were injected on Day 0. IL-2 or IL-2 vehicle was administered by bolus injection, two injections give 6 hours apart each day, Day 1 through Day 4. Biomed 101 or Biomed 101 vehicle was administered by intraperitoneal injection. Biomed 101 or vehicle was administered 15 minutes prior to each IL-2 injection. An additional group of 15 untreated control mice was used for timing the termination of the study. At Day 10, three untreated control mice were to be euthanized each day until tumor burden was determined to be optimal for counting metastatic foci, at which time the remaining rumored and five non-rumored mice were to be euthanized and lungs removed for determination of body weights, lung weights and numbers of metastatic foci.

Statistical analysis

Anti-tumor activity was assessed by counts of metastatic foci in the lungs. Comparison among the three treatment groups (Groups 1, 2 and 3) was performed using one-way ANOVA (or Kruskal-Wallis one-way analysis of variance on ranks for data with non-normal distribution) with the three between-group comparisons performed using adjustment for multiple comparisons.

Results

All dosage regimens appeared to be well-tolerated. However, there was one death in Group 2 (Proleukin alone) on Day 4. The combination of Biomed 101 and Proleukin (Group 3) resulted in a weight loss of 11% on Day 4. The mice from each treatment group (Groups 1, 2 and 3), the fifteen untreated control mice and five non-tumored untreated mice were euthanized on Day 10 and their lungs removed. The lungs were weighed and the number of lung metastases counted.

The number of lung metastases was significantly lower in Groups 2 and 3 than in the vehicle control Group 1 (one-way ANOVA with Student-Newman-Keuls method for multiple comparisons). The mean number of lung metastases was numerically lower in the Biomed 101 treated group (56) than in the group receiving IL-2 alone (66), although the difference was not statistically significant (Wilcoxon). The effects of each treatment are summarized in Table 2 below.

The lung weights were not normally distributed. One-way analysis of ranks was performed using Kruskal-Wallis test. IL-2 alone did not decrease the lung weights compared with vehicle control. The combination of Biomed 101 and IL-2 resulted in significantly lower lung weights than treatment with IL-2 alone (Dunn's method for multiple comparisons). The results are summarized in Table 2 below.

TABLE 4

Effect of Treatment on Lung Metastases and Lung

| Group # (N) | Test Articles | Number of lung mets Mean (± SEM) | Median Lung Weight (mg) |
|---|---|---|---|
| Group 1 (20) | Biomed 101 vehicle IL-2 vehicle | 98 (±9) | 174 |
| Group 2 (19) | Biomed 101 vehicle IL-2 | 66* (±6) | 177 |
| Group 3 (20) | Biomed 101 IL-2 | 56* (±5) | 167** |

*p < 0.05 compared with Group 1, Student-Newman-Keuls method
**p < 0.13 compared with Group 2, Wilcoxon/Kruskal-Wallis The mean number of lung metastases was significantly lower in the group of animals treated with IL-2 than in the vehicle control group: 66 vs.98. The group of animals treated with Biomed 101 in addition to IL-2 had a significantly lower mean number of lung metastases than the vehicle control group (56 vs. 98) and a lower mean number of metastases than the group treated with IL-2 alone (56 vs. 66) although the difference between the two groups receiving IL-2 was not statistically significant. Thus, the coadiminstration of the leukotriene receptor antagonist Biomed 101 fully preserves and may enhance the anti-tumor activity of IL-2. Taken together, then, the data from Example 4 and Example 5 demonstrate that the combination of Biomed 101 and IL-2 is superior to IL-2 alone, by improving specifically and uniquely the therapeutic index of IL-2.

EXAMPLE 6

This example explains how a compound of Formula (I) is administered to humans to increase the number of antitumor doses of IL-2 that can be administered and well tolerated while preventing the increase in IL-2-induced adverse effects that are typically associated with increasing doses of IL-2.

Test material

A preferred LA compound (as defined in Example 3) from drug substance lot # BA901 was supplied as 25 mg capsules Batch # 99G111 by BioMedicines, Inc. Each hard gelatin capsule contained 25 mg LA plus excipients including lactose hydrous NF; hydroxypropylmethylcellulose 2910, 6 cps USP; sodium lauryl sulfate NF; purified water, USP; and sodium chloride.

Patients

Patients meeting the following criteria are eligible for treatment with the LA and IL-2:
  Men or women age 18 years or older
  Pathologically confirmed renal cell carcinoma
  ECOG performance status 0 or 1 and predicted life expectancy of 12 weeks or more
  For women, childbearing potential definitively terminated by surgery, radiation or menopause or child-bearing potential attenuated by use of an approved contraceptive method (IUD, oral contraceptive, or double-barrier device)
  For women capable of becoming pregnant, negative serum beta-HCG pregnancy test within 7 days prior to initiation of Biomed 101 therapy Patients meeting any of the following criteria are ineligible for treatment with LA:
  History of:
    Significant neurological dysfunction including seizures, uncontrolled central nervous systemic metastases, or clinical signs of other significant neurological diseases
  Active gastrointestinal bleeding
  Signs of hepatic failure including encephalopathy
  History of moderate or severe coronary artery disease (NYHA Class 3 or 4)
  Renal insufficiency (serum creatinine>2.0 mg/dL)
  Aspartate aminotransferase, alanine aminotransferase or serum bilirubin levels more than 2.5 times upper limit of normal
  Hemoglobin<9 g/dL
  A platelet count of less than 100,000 platelets per $mm^3$
  A total white blood cell count of less than 2,000 cells per mm3
  Any concurrent infectious disease requiring antimicrobial treatment
  Pregnant or lactating females
  Usage of an investigational drug within the thirty (30) days prior to enrollment; or the planned usage of an investigational drug other than Biomed 101 during the course of the current study.
  Prior treatment with the preferred LA in the setting of this clinical trial.

Dosing

Patients received IL-2 600,000 IU/kg by intravenous bolus three times daily during 5 days for a planned total of 14 doses. LA was administered orally 1 hour prior to each schedule dose of IL-2 as well as 8 hours after the final scheduled dose. If dose of IL-2 was withheld because of IL-2 induced toxicity, dosing with LA continued. Doses of LA ranged from 25 mg three times daily (TID) to 75 mg TID. Plasma levels of LA were obtained at each dose level.

Clinical Endpoints

The principal activity endpoint was the relationship between the total number of doses of IL-2 that could be administered and well tolerated by patients and the plasma levels of LA. A second endpoint was the response rate in patients of the tumor to the combination therapy with the leukotriene $B_4$ receptor antagonist and IL-2 as judged by complete responses (total disappearance of measurable tumor) or partial responses (a $\geq 50\%$ decrease in measurable tumor volume).

Analysis of Data

Data were analyzed by examining the significance of the correlation between number of doses of IL-2 and LA plasma level (Spearman's rho).

Results of Clinical Trial

The plasma level of LA increased as the total daily dose of LA increased. As the dose of LA was increased, and the plasma level of LA rose, the total number of doses of IL-2 that could be well tolerated by patients also rose (Spearman's rho=0.47, p<0.03). Similarly, the number of doses of IL-2 that were required to be withheld because of IL-2 toxicity decreased as the plasma level of LA increased. In addition, the objective response rate in these patients was 27.3% (despite no increase in the incidence of side effects). This objective response rate is significantly higher than the 8–10% historically noted with Il-2 treatment alone. Moreover, this response rate of 27.3% is comparable to the objective response rate noted in patients treated with the combination of IL-2 and alpha interferon but for which the [IL-2+interferon] side effect rate is far higher than for IL-2 alone. Thus the combination of IL-2+Biomed 101 is uniquely superior to both monotherapy with IL-2 alone or with other combination therapy such as IL-2+alpha interferon.

What is claimed is:

1. A method of mitigating an adverse pharmacological effect of IL-2 when administered to a human as part of the treatment of a malignancy or a viral disease, which method comprises administering to the human an amount of a leukotriene $B_4$ ($LTB_4$) antagonist that is sufficient to mitigate the adverse effect.

2. The method of claim 1, wherein the $LTB_4$ antagonist is a $LTB_4$ receptor antagonist.

3. The method of claim 2, wherein the $LTB_4$ receptor antagonist mitigates the IL-2-induced adverse effects while preserving or enhancing the antitumor, antiviral, or immunostimulatory effects of IL-2.

4. The method of claim 2, wherein the $LTB_4$ receptor antagonist reduces the IL-2-induced adverse effects more than any reduction in IL-2 related antitumor, antiviral, or immunostimulatory effects of IL-2.

5. The method of claim 2, wherein the adverse pharmacological effect is increased vascular permeability.

6. The method of claim 5, wherein the signs and symptoms of the adverse pharmacological effect include edema, systemic hypotension, reduced organ perfusion, or dysfunction of one or more organs, tissues or cells of the subject body.

7. The method of claim 2, wherein the leukotriene $B_4$ receptor antagonist is represented by the formula (I)

or a stereoisomer or a pharmaceutically acceptable salt thereof, wherein $R^1$ represents hydrogen, alkyl having 2 to 6 carbon atoms, alkenyl having 2 to 6 carbon atoms, alkynyl having 2 to 6 carbon atoms, or $(CH_2)_nR$ wherein R represents cycloalkyl of 3 to 5 carbon atoms and n is 1 or 2;

$R^2$ represents hydrogen, methyl or ethyl;

$R^3$ represents alkyl having 1 to 5 carbon atoms;

W represents $(CH_2)_x$ where x is 2 to 7, alkenylene having 3 to 7 carbon atoms, alkynylene having 3 to 7 carbon atoms or cyclopentylene;

$R^4$ represents hydrogen, alkyl having 2 to 5 carbon atoms, alkynyl having 2 to 5 carbon atoms, alkenyl having 2 to 5 carbon atoms, alkanoyl of 2 to 5 carbon atoms or aralkanoyl of 7 to 9 carbon atoms;

$R^5$ represents hydrogen, alkyl having 1 to 6 carbon atoms, or $R^5$ represents alkanoyl having 2 to 4 carbon atoms, or $(CH_2)_y$—$CO_2R^8$ wherein Y is 0 to 4 and $R^8$ is hydrogen or alkyl having 1 to 6 carbon atoms;

$R^6$ represents hydrogen or together with $R^5$ represents a carbon to carbon bond; and A represents —Z—$CO_2R^7$ wherein $R^7$ represents hydrogen or alkyl having 1 to 6 carbon atoms, and wherein Z is absent or represents straight or branched chain alkylene or alkenylene having up to 6 carbon atoms.

8. The method of claim 7, wherein the leukotriene $B_4$ receptor antagonist is represented by Formula (I) and $R^1$ represents alkyl having 2 to 4 carbon atoms;

$R^2$ represents hydrogen, methyl or ethyl;

$R^3$ represents alkyl having 1 to 3 carbon atoms;

W represents $(CH_2)_x$ where x is 3 to 5, alkenylene having 3 to 5 carbon atoms, alkynylene having 3 to 5 carbon atoms, or cyclopentylene;

$R^4$ represents alkyl having 2 to 4 carbon atoms, acetyl or benzoyl;

$R^5$ represents hydrogen or alkyl having 1 to 4 carbon atoms;

$R^6$ represents hydrogen; and

A represents —Z—$CO_2R^7$, wherein $R^7$ represents hydrogen or alkyl having 1 to 4 carbon atoms, and wherein Z is absent or represents alkylene having up to 2 carbon atoms.

9. The method of claim 8, wherein the leukotriene $B_4$ receptor antagonist is represented by Formula (I) and $R^1$ is n-propyl;

$R^2$ and $R^3$ each is methyl;

W is $(CH_2)_x$, where x is 3,4 or 5;

$R^4$ is 8-n-propyl;

$R^5$ represents hydrogen or alkyl of 1 to 4 carbon atoms; and

A represents —Z—$CO_2R^7$ wherein $R^7$ represents hydrogen or alkyl having 1 to 4 carbon atoms and Z is absent or represents alkylene having up to 2 carbon atoms.

10. The method of claim 9, wherein the leukotriene $B_4$ receptor antagonist is represented by Formula (I) and W is $(CH_2)_3$, $R^5$ is H and A is $(CH_2)_p$—COOH where p is 0,1 or 2.

11. The method of claim 10, wherein the leukotriene $B_4$ antagonist is represented by Formula (I) and A is —$CO_2H$.

12. The method of claim 8, wherein $R^1$ is n-propyl, $R^2$ is hydrogen, $R^3$ is methyl, W is $(CH_2)_5$, $R^4$ is 6-acetyl, $R^5$ is hydrogen, and A is COOH.

13. A method of treating a malignancy or a viral disease in a subject, which method comprises administering a therapeutically effective amount of IL-2 in conjunction with a leukotriene $B_4$ ($LTB_4$) antagonist in an amount sufficient to reduce IL-2-induced adverse pharmacological effects.

14. The method of claim 13, wherein the $LTB_4$ antagonist is a $LTB_4$ receptor antagonist.

15. The method of claim 14, wherein the $LTB_4$ receptor antagonist reduces the IL-2-induced adverse effects, while preserving or enhancing the antitumor, antiviral, or immunostimulatory effects of IL-2.

16. The method of claim 14, wherein the $LTB_4$ receptor antagonist reduces the IL-2-induced adverse effects more than any reduction in IL-2 related antitumor, antiviral, or immunostimulatory effects of IL-2.

17. The method of claim 14, wherein the adverse pharmacological effect is increased vascular permeability.

18. The method of claim 17, wherein the signs and symptoms of the adverse pharmacological effect include one or more of edema, systemic hypotension, reduced organ perfusion, or dysfunction of one or more organs, tissues or cells of the subject's body.

19. The method of claim 14, wherein the leukotriene $B_4$ receptor antagonist is represented by the formula (I)

or a stereoisomer or a pharmaceutically acceptable salt thereof wherein $R^1$ represents alkyl having 2 to 6 carbon atoms, alkenyl having 2 to 6 carbon atoms, alkynyl having 2 to 6 carbon atoms, or $(CH_2)_nR$ wherein R represents cycloalkyl of 3 to 5 carbon atoms and n is 1 or 2;

$R^2$ represents hydrogen, methyl or ethyl;

$R^3$ represents alkyl having 1 to 5 carbon atoms;

W represents $(CH_2)_x$ where x is 2 to 7, alkenylene having 3 to 7 carbon atoms, alkynylene having 3 to 7, or cyclopentylene;

$R^4$ represents hydrogen, alkyl having 2 to 5 carbon atoms, alkenyl having 2 to 5 carbon atoms, alkenyl having 2 to 5 carbon atoms, alkanoyl of 2 to 5 carbon atoms, or aralkanoyl of 7–9 carbon atoms;

$R^5$ represents hydrogen, alkyl having 1 to 6 carbon atoms, or $R^5$ represents alkanoyl having 2 to 4 carbon atoms, or $(CH_2)_y$—$CO^2R^8$ wherein y is 0 to 4 and $R^8$ is hydrogen or alkyl having 1 to 6 carbon atoms;

$R^6$ represents hydrogen or together with $R^5$ represents a carbon to carbon bond; and A represents —Z—$CO_2R^7$ wherein $R^7$ represents hydrogen or alkyl having 1 to 6 carbon atoms, and wherein Z is absent or represents straight or branched chain alkylene or alkenylene having up to 6 carbon atoms.

20. The method of claim 19, wherein the leukotriene $B_4$ receptor antagonist is represented by Formula (I) and $R^1$ represents alkyl having 2 to 4 carbon atoms;

$R^2$ represents hydrogen, methyl or ethyl;

$R^3$ represents alkyl having 1 to 3 carbon atoms;

W represents $(CH_2)_x$ where x is 3 to 5, alkenylene having 3 to 5 carbon atoms, alkynylene having 3 to 5 carbon atoms, or cyclopentylene;

$R^4$ represents alkyl having 2 to 4 carbon atoms, acetyl or benzoyl;

$R^5$ represents hydrogen or alkyl having 1 to 4 carbon atoms;

$R^6$ represents hydrogen; and

A represents —Z—$CO_2R^7$, wherein $R^7$ represents hydrogen or alkyl having 1 to 4 carbon atoms, and wherein Z is absent or represents alkylene having up to 2 carbon atoms.

21. The method of claim 20, wherein the leukotriene $B_4$ receptor antagonist is represented by Formula (I) and $R^1$ is n-propyl;

$R^2$ and $R^3$ each is methyl;

W is $(CH_2)_x$, where x is 3, 4 or 5;

$R^4$ is 8-n-propyl;

$R_5$ represents hydrogen or alkyl of 1 to 4 carbon atoms; and

A represents —Z—$CO_2R^7$ wherein $R^7$ represents hydrogen or alkyl having 1 to 4 carbon atoms and Z is absent or represents alkylene having up to 2 carbon atoms.

22. The method of claim 21, wherein the leukotriene $B_4$ receptor antagonist is represented by Formula (I) and W is $(CH_2)_3$, $R^5$ is H and A is $(CH_2)_p$—COOH where p is 0, 1 or 2.

23. The method of claim 22, wherein the leukotriene $B_4$ antagonist is represented by Formula (I) and A is —COOH.

24. The method of claim 20, wherein $R^1$ is n-propyl, $R^2$ is hydrogen, $R^3$ is methyl, W is $(CH_2)_5$, $R^4$ is 6-acetyl, $R^5$ is hydrogen, and A is COOH.

25. The method of claim 14, wherein the IL-2 and the leukotriene $B_4$ receptor antagonist are administered in combination as a unit dosage.

26. The method of claim 14, wherein the IL-2 and the leukotriene $B_4$ receptor antagonist are administered individually.

27. The method of claim 26, wherein the leukotriene $B_4$ receptor antagonist is administered orally before, during or after the IL-2 is administered.

* * * * *

UNITED STATES PATENT AND TRADEMARK OFFICE
CERTIFICATE OF CORRECTION

PATENT NO. : 6,423,744 B2
DATED : July 23, 2002
INVENTOR(S) : Stanford Mark Moran It is certified that error appears in the above-identified patent and that said Letters Patent is hereby corrected as shown below:

<u>Title page,</u>
Item [73], should read as follows:
-- BioMedicines, Inc. --

Signed and Sealed this

Fifth Day of November, 2002

*Attest:*

*Attesting Officer*

JAMES E. ROGAN
*Director of the United States Patent and Trademark Office*